(12) United States Patent
Maeda et al.

(10) Patent No.: US 6,660,730 B2
(45) Date of Patent: Dec. 9, 2003

(54) ANHYDROUS MIRTAZAPINE AND PROCESS FOR PREPARING THE SAME

(75) Inventors: Chiharu Maeda, Osaka (JP);
Sadanobu Yoshikawa, Osaka (JP);
Eiichi Iishi, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 4 days.

(21) Appl. No.: 09/842,871

(22) Filed: Apr. 27, 2001

(65) Prior Publication Data

US 2002/0065413 A1 May 30, 2002

(30) Foreign Application Priority Data

Nov. 27, 2000 (JP) ........................................ 2000-359891

(51) Int. Cl.⁷ ............................................. C07D 471/14
(52) U.S. Cl. .................. 514/214.02; 540/578
(58) Field of Search ...................... 540/578; 514/214.02

(56) References Cited

U.S. PATENT DOCUMENTS 4,062,848 A    12/1977   Van Der Burg ............. 260/268

FOREIGN PATENT DOCUMENTS

WO          WO 00/62782        * 10/2000

* cited by examiner

*Primary Examiner*—Richard L. Raymond
*Assistant Examiner*—Hong Liu
(74) *Attorney, Agent, or Firm*—Oblon, Spivak, McClelland, Maier & Neustadt, P.C.

(57) ABSTRACT

Methods for producing anhydrous mirtazapine crystals that are either (1) substantially free of lower alcohol insolubles or (2) substantially free of residual solvent and have an average particle diameter of from 10 to 50 μm, are provided, and the resulting anhydrous mirtazapine crystals produced thereby, which are useful in pharmaceuticals.

39 Claims, 1 Drawing Sheet

40 μm

ANHYDROUS MIRTAZAPINE AND PROCESS FOR PREPARING THE SAME

BACKGROUND OF THE INVENTION

1. Field of the Invention

The present invention relates to anhydrous mirtazapine and a process for preparing the same.

2. Discussion of the Background

U.S. Pat. No. 4,062,848 discloses a process for increasing the purity of mirtazapine, (a useful antidepressant), by recrystallizing mirtazapine from a petroleum ether or similar subject.

However, in performing this process, impurities are precipitated in an oily state when crude mirtazapine having a purity of about 95 to 99% is used, so that the crystallization of mirtazapine is inhibited, and makes it difficult to crystallize mirtazapine having a high purity.

Accordingly, there is a significant need for a process capable of efficiently and industrially preparing anhydrous mirtazapine having a high purity from crude mirtazapine.

SUMMARY OF THE INVENTION

Accordingly, one object of the present invention is to provide a process capable of efficiently preparing an anhydrous mirtazapine crystal substantially free of lower alcohol insolubles.

A further object of the present invention is to provide a method for the production of anhydrous mirtazapine having an average particle diameter of 10 to 50 $\mu$m and substantially free of residual solvent.

These and other objects of the present invention have been satisfied by the discovery of a process for preparing an anhydrous mirtazapine crystal, comprising filtering a lower alcohol solution of crude mirtazapine to provide a filtrate; concentrating the filtrate to provide a concentrated filtrate; and crystallizing anhydrous mirtazapine from the concentrated filtrate using a precipitation solvent selected from the group consisting of heptane and petroleum ethers and the anhydrous mirtazapine crystal produced thereby which is substantially free of lower alcohol insolubles.

In a further embodiment, the present invention relates to the discovery of a process for the production of anhydrous mirtazapine crystal that is substantially free of residual solvent, by pulverizing the anhydrous mirtazapine to an average particle diameter of from 10 to 50 $\mu$m, and the anhydrous mirtazapine crystal produced thereby.

BRIEF DESCRIPTION OF THE DRAWINGS

Various other objects, features and attendant advantages of the present invention will be more fully appreciated as the same becomes better understood from the following detailed description when considered in connection with the accompanying figure, wherein.

DETAILED DESCRIPTION OF THE PREFERRED EMBODIMENTS

Figure 1:
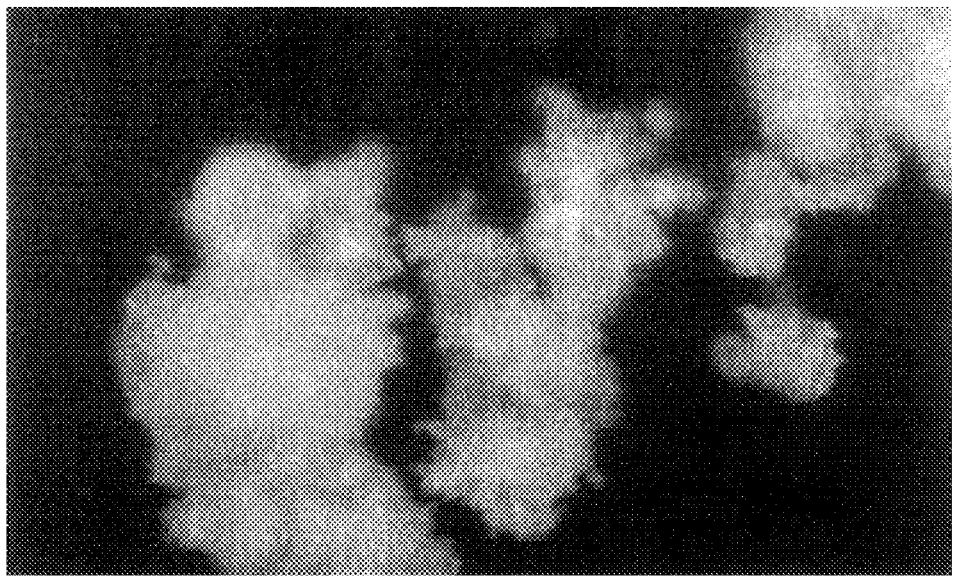
FIG. 1 is a microphotograph of the anhydrous mirtazapine crystals obtained in Example 1 of the present invention (magnification: 500).
Figure 1:
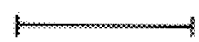

The present invention relates to:

(1) an anhydrous mirtazapine crystal substantially free of lower alcohol insolubles;

(2) a process for preparing an anhydrous mirtazapine crystal substantially free of lower alcohol insolubles, comprising (a) filtering a lower alcohol solution of crude mirtazapine, (c) concentrating a filtrate obtained thereby, and (d) crystallizing anhydrous mirtazapine with a precipitation solvent selected from the group consisting of heptane and a petroleum ether;

(3) anhydrous mirtazapine having an average particle diameter of 10 to 50 $\mu$m and substantially free of residual solvent; and (4) a process for preparing anhydrous mirtazapine having an average particle diameter of 10 to 50 $\mu$m and substantially free of residual solvent, comprising pulverizing anhydrous mirtazapine crystal to an average particle diameter of 10 to 50 $\mu$m.

The anhydrous mirtazapine crystal of the present invention refers to a crystal that either is (1) substantially free of lower alcohol insolubles or (2) substantially free of residual solvent and has an average particle diameter of 10 to 50 $\mu$m.

The lower alcohol used in the process of the present invention can be any alcohol having from 1 to 4 carbons, and preferably includes, but is not limited to, methanol, ethanol, propanol, and isopropanol. Among these lower alcohols, methanol is more preferred, in order to provide better removability of alcohol insolubles and economics. In the lower alcohol, water can be contained in an amount of 1 to 5% by weight.

The term "substantially free of lower alcohol insolubles" as referred to herein means that the absorbance of a methanol solution of mirtazapine, prepared by adding 1 part by volume of anhydrous mirtazapine crystal to 10 parts by volume of methanol, and dissolving the anhydrous mirtazapine crystal in the methanol at a temperature of 20° to 30° C., is not more than 0.1 at a wavelength of 600 nm.

As a starting material for the process of the present invention, any crude mirtazapine can be used.

The crude mirtazapine can be preferably prepared, for instance, by a process disclosed in U.S. Pat. No. 4,062,848.

More preferably, the crude mirtazapine is obtained by subjecting 2-(4-methyl-2-phenylpiperazin-1-yl)pyridine-3 (hereinafter referred to as pyridinemethanol compound) to dehydration and ring closure by using concentrated sulfuric acid.

As the concentrated sulfuric acid, a concentrated sulfuric acid having a concentration of 97 to 99% is preferably used. It is desired that the temperature of the concentrated sulfuric acid (when the pyridinemethanol compound is added to the concentrated sulfuric acid) is 0° to 40° C., preferably 5° to 35° C., in order to suppress heat generation and generation of tarred impurities.

In the case where the pyridinemethanol compound is added to the concentrated sulfuric acid, it is preferred that the pyridinemethanol compound is added in divided portions to the concentrated sulfuric acid, in order to cause the reaction to proceed efficiently. For instance, it is preferred that the pyridinemethanol compound is added to the concentrated sulfuric acid in 5 to 20 divided portions.

It is also preferred that the amount of the concentrated sulfuric acid is 30 to 400 parts by weight, preferably 350 to 400 parts by weight based on 100 parts by weight of the pyridinemethanol compound.

After the addition of the pyridinemethanol compound to the concentrated sulfuric acid, it is preferred to stir the mixture at a temperature of from about 20° to about 50° C., preferably 30° to 40° C. for about 7 to about 10 hours, in order to accelerate the reaction.

Thus, the pyridinemethanol compound is subjected to dehydration and ring closure. The end point of the ring closure reaction can be confirmed by HPLC (high-performance liquid chromatography).

It is then preferred to lower the concentration of sulfuric acid, for instance, by the addition of a thin stream of the reaction solution to water. It is preferred that the amount of water is 100 to 200 parts by weight based on 100 parts by weight of the reaction solution, from the viewpoint of operability. In addition, it is preferred that the liquid temperature of the reaction solution during the addition is from 0° to 30° C., in order to suppress heat generation and generation of impurities, i.e. tarred products.

It is further preferred that aqueous alkali is added to the reaction solution to neutralize the excess acid. Any alkali can be used, including but not limited to, sodium hydroxide, potassium hydroxide and sodium carbonate. Among them, sodium hydroxide is preferred. It is preferred that the concentration of the alkali hydroxide in the aqueous alkali is 20 to 30% by weight, more preferably 20 to 25% by weight, from the viewpoint of operability. The amount of the aqueous alkali hydroxide is preferably adjusted so that the pH of the reaction solution becomes 1 to 3, more preferably 1 to 2, in order not to precipitate crystals.

After the adjustment of the pH, decolorizing carbon is preferably added to the solution for decolorizing the solution.

The crude mirtazapine can then be extracted by filtering the solution as needed, and adding toluene to the filtrate.

Toluene is used for removing oil-soluble impurities contained in the filtrate. The amount of toluene is preferably from 80 to 200 parts by weight, more preferably 100 to 150 parts by weight based on 100 parts by weight of the pyridinemethanol compound. The temperature of the solution of toluene added to the filtrate is preferably 15° to 35° C., more preferably 20° to 30° C. Also, the solution is preferably stirred for not less than 15 minutes, more preferably 30 minutes to 1 hour.

The mixture is then separated into two layers, an organic layer and an aqueous layer, by allowing the solution to stand for not less than 30 minutes, preferably 1 to 2 hours.

Toluene is then added to the separated aqueous layer. The amount of toluene is preferably 150 to 300 parts by weight, more preferably 170 to 250 parts by weight based on 100 parts by weight of the pyridinemethanol compound, in order to provide efficient extraction of the crude mirtazapine. After the addition of toluene, the pH of the aqueous layer is preferably adjusted to not less than 8, more preferably 8 to 10. The pH of the aqueous layer can be adjusted with an alkali. The alkali includes, for instance, an aqueous sodium hydroxide or other alkali as disclosed above.

The resulting solution is preferably heated to a temperature of 70° to 85° C., more preferably 75° to 80° C., in order to dissolve the crude mirtazapine and improve separability into layers.

When the solution is allowed to stand, the solution separates into two layers. A dehydrating agent is preferably added to the organic layer, in order to remove moisture therefrom. The dehydrating agent can be any conventional dehydrating agent, including but not limited to, anhydrous magnesium sulfate, and anhydrous sodium sulfate. Anhydrous magnesium sulfate is more preferred, from the viewpoint of dehydration efficiency. The amount of the dehydration agent is preferably 5 to 50 parts by weight, more preferably 10 to 20 parts by weight based on 100 parts by weight of the pyridinemethanol compound.

The dehydrating agent can also be precoated on a filter used for filtering the organic layer, if desired.

In addition, a decolorizing agent is also preferably added to the organic layer, in order to improve the hue and increase the purity of the resulting anhydrous mirtazapine crystals.

The decolorizing agent can be any conventional decolorizing agent, including but not limited to, activated alumina and decolorizing carbon. Among them, activated alumina is most preferred. Although the amount of the decolorizing agent cannot be absolutely determined because the amount would differ depending upon the specific agent chosen, the amount of the decolorizing agent is preferably 5 to 50 parts by weight, more preferably 10 to 20 parts by weight based on 100 parts by weight of the pyridinemethanol compound.

The temperature at which the anhydrous mirtazapine crystal is subjected to decolorization is not particularly limited. The decolorization temperature is preferably in the range of from room temperature (approx. 20–25° C.) to 85° C., more preferably from 30° to 80° C. The time period required for decolorization is preferably from 15 to 30 minutes.

Toluene is preferably distilled from the organic layer. The amount of toluene distilled can be 50 to 80% by weight, preferably 60 to 70% by weight of the toluene used. The distillation of toluene can be carried out by any distillation means, preferably by distillation under reduced pressure. The reduced pressure during such a reduced pressure distillation is preferably 0.6 to 40 kPa, more preferably 4 to 30 kPa, in order to improve the concentration rate. Also, the distillation temperature is preferably 30° to 85° C., more preferably 60° to 75° C., to improve the concentration rate and prevent or minimize coloration of the resulting anhydrous mirtazapine crystals.

Heptane is preferably added to the resulting concentrate in order to crystallize the crude mirtazapine. The amount of heptane is preferably 450 to 700 parts by weight, more preferably 500 to 600 parts by weight based on 100 parts by weight of the pyridinemethanol compound, in order to increase the crystallization yield. The temperature at which heptane is added is preferably 75° to 85° C., to improve filterability. When heptane is added, the heptane is preferably added in a thin stream.

The resulting solution is preferably then gradually cooled to a temperature of −10° to 5° C. over a period of time of 1 to 5 hours, more preferably 2 to 3 hours, in order to provide crystal diameters of relatively consistent size and increase the yield.

Thus, the crude mirtazapine can be crystallized. The resulting crystals can be washed with a cooled solvent, preferably cooled to 0° to 5° C. The solvent can be, for instance, heptane or a mixed solvent of toluene and heptane. In the case where a mixed solvent is used, the ratio of heptane to toluene can be preferably adjusted so that the amount of heptane is 70 to 100 parts by weight, based on 100 parts by weight of toluene.

The crystals can be dried, preferably under reduced pressure at a temperature of 45° to 65° C., more preferably 50° to 60° C., as needed.

Thus, the crude mirtazapine is obtained.

The anhydrous mirtazapine crystal is obtained by filtering a lower alcohol solution of the crude mirtazapine, concentrating the filtrate, and crystallizing from a solvent selected from the group consisting of heptane and petroleum ethers. The anhydrous mirtazapine crystal thus obtained is substantially free of alcohol insolubles.

The lower alcohol solution of crude mirtazapine can be provided by any method, such as, dissolving crude mirtazapine in a lower alcohol. Within the context of the present invention, the term "lower alcohol" refers to $C_1$–$C_4$ alcohols, as noted above.

The lower alcohol preferably includes, but is not limited to, methanol, ethanol, propanol, isopropanol. Among those lower alcohols, methanol is most preferred, from the viewpoints of removability of alcohol insolubles and economics. It is preferred that the amount of the lower alcohol is 300 to 500 parts by weight, preferably 350 to 450 parts by weight based on 100 parts by weight of the crude mirtazapine, to provide better dissolution the crude mirtazapine in the lower alcohol and to better avoid dissolving impurities contained in the crude mirtazapine.

The temperature at which the crude mirtazapine is dissolved in the lower alcohol is preferably −5° to 10° C., more preferably 0° to 5° C., in order to shorten the time period required for dissolving the crude mirtazapine and to better avoid dissolving impurities contained in the crude mirtazapine.

After the crude mirtazapine is dissolved in the lower alcohol, the resulting solution is preferably contacted with a decolorizing agent in order to decolorize the crude mirtazapine. A preferred process for contacting the solution with the decolorizing agent includes, but is not limited to, adding a decolorizing agent to the solution; or placing a decolorizing agent on the surface of a filter in a filtering device, and pouring the solution over the filtering device and through the decolorizing agent.

The decolorizing agent can be any conventional decolorizing agent, including but not limited to, decolorizing carbon, activated alumina, and activated clay. Among them, a combined use of decolorizing carbon and activated alumina is preferred, in order to provide better decolorization.

The amount of the decolorizing agent is preferably 0.1 to 30 parts by weight, more preferably 0.5 to 25 parts by weight based on 100 parts by weight of the crude mirtazapine, to sufficiently decolorize the crude mirtazapine and improve the purity. In addition, in the case where decolorizing carbon is used together with activated clay, the amount of the decolorizing carbon is preferably 0.1 to 0.5 parts by weight and that the amount of the activated clay is preferably 10 to 25 parts by weight, based on 100 parts by weight of the crude mirtazapine.

The present process involves filtering the lower alcohol solution of the crude mirtazapine. The filtration method is not particularly limited, but can use any conventional filtration methods, including but not limited to, reduced pressure filtration methods and pressure filtration methods. By carrying out the filtration, the lower alcohol insolubles contained in the solution are separated and removed. Accordingly, the primary requirement is that the filtration medium be sufficient in terms of permeability and filtration ability to remove the lower alcohol insolubles.

The temperature at which the filtration is carried out is preferably −5° to 10° C., more preferably 0° to 5° C., to provide less solubility of the lower alcohol insolubles and more solubility of the crude mirtazapine.

The lower alcohol insolubles are removed from the resulting filtrate, and the crude mirtazapine remaining dissolved in the filtrate. The filtrate is then preferably concentrated under reduced pressure. This concentration is preferably carried out at a temperature of from 0° to 50° C., in order to provide better stability of the anhydrous mirtazapine and to avoid coloration of anhydrous mirtazapine. In addition, the concentration step is preferably carried out until the temperature of the filtrate reaches 50° C.

Next, in order to precipitate anhydrous mirtazapine contained in the concentrate, a precipitation solvent selected from the group consisting of heptane and petroleum ethers is added to the filtrate. Among those precipitation solvents, heptane is preferred. The amount of the precipitation solvent is preferably 100 to 1000 parts by weight, more preferably 130 to 800 parts by weight, most preferably 130 to 700 parts by weight based on 100 parts by weight of the crude mirtazapine used, in order to prevent or minimize precipitation of anhydrous mirtazapine in an oily state and to increase the yield of anhydrous mirtazapine.

The dissolved anhydrous mirtazapine is then crystallized by distilling solvent contained in the solution, obtained in the above step of adding the precipitation solvent to the concentrate, under normal pressure. During the crystallization, the liquid temperature of the solution is preferably 50 to 60° C. Additionally, methanol is preferably distilled until the internal temperature of the solution reaches from 65° to 80° C., more preferably 75° to 80° C.

After the solvent is distilled off from the above-mentioned solution, anhydrous mirtazapine crystals can be precipitated by cooling the solution preferably to −10° to 5° C. After cooling the solution, the solution is preferably stirred at −10° to 5° C. for about 1 to about 5 hours, to increase the yield of the anhydrous mirtazapine crystal.

The anhydrous mirtazapine crystals can preferably be collected by filtration. The collected anhydrous mirtazapine crystals can be dried, preferably under reduced pressure. In such a case, the drying temperature is preferably 20° to 60° C., more preferably 40° to 60° C., to reduce the residual solvent in the anhydrous mirtazapine crystals and prevent coloration of the anhydrous mirtazapine crystals. In addition, the reduced pressure of the drying step is preferably 0.1 to 40 kPa, more preferably 0.1 to 4 kPa, to substantially remove the residual solvent in the anhydrous mirtazapine crystal and improve drying rate.

In order to obtain anhydrous mirtazapine crystals having a higher purity, purification using a lower alcohol, such as methanol, and recrystallization using the above-mentioned precipitation solvent can be repeatedly carried out, as desired.

The anhydrous mirtazapine crystal thus obtained is substantially free of lower alcohol insolubles. The particle diameter of the resulting anhydrous mirtazapine crystal is too large to be measured with a laser diffraction particle size analyzer. The particle diameter is preferably 10 to 300 μm.

The anhydrous mirtazapine substantially free of residual solvent can be obtained by pulverizing the anhydrous mirtazapine crystal. As described above, when the anhydrous mirtazapine crystal is pulverized, surprisingly, the anhydrous mirtazapine obtained is substantially free of residual solvent.

The term "substantially free of residual solvent" as referred to herein means that the amount of residual solvent in the anhydrous mirtazapine is not more than 200 ppm.

The pulverization of the anhydrous mirtazapine crystal can be carried out using any conventional pulverizing means, including but not limited to, a hammer-mill, a cutter mill, or an atomizer.

The average particle diameter of the anhydrous mirtazapine after pulverization is preferably 10 to 50 μm, for ease in preparations and handling. In the present specification, the average particle diameter of the anhydrous mirtazapine can be determined by a laser diffraction particle size analyzer, commercially available from Shimadzu Corporation under the trade name of SALD 1100, medium: water.

The anhydrous mirtazapine crystal substantially free of lower alcohol insolubles and the anhydrous mirtazapine having an average particle diameter of 10 to 50 μm and substantially free of residual solvent are useful as antidepressants.

EXAMPLES

Having generally described this invention, a further understanding can be obtained by reference to certain specific examples which are provided herein for purposes of illustration only and are not intended to be limiting unless otherwise specified.

Preparation Example 1

Preparation of Crude Mirtazapine

A 10 L flask was charged with 6202 g of concentrated sulfuric acid, and thereafter 1723 g of 2-(4-methyl-2-phenylpiperazin-1-yl)pyridine-3-methanol was added to the flask in divided portions at 5° to 30° C., and the mixture was stirred at 30° to 40° C. for 8 hours.

The resulting reaction mixture was added in a thin stream to 12.4 kg of water at 0° to 5° C. to dissolve the reaction mixture in water. The inside of the flask was washed with 770 g of concentrated sulfuric acid, and the washed liquid was mixed with a reaction mixture obtained above.

Next, the pH of this reaction solution was adjusted to about 1.6 with 25% by weight aqueous sodium hydroxide, and 164 g of decolorizing carbon was added to the reaction mixture. The mixture was stirred for 1 hour, and thereafter filtered. The decolorizing carbon was washed with 1.6 kg of water, and the washed solution was mixed with the filtrate.

To the filtrate was added 2988 g of toluene, and the mixture was extracted at 25° to 35° C. to remove insolubles.

The solution was allowed to separate into an aqueous layer and an organic layer at 20° to 30° C. To the aqueous layer was added 2988 g of toluene, and the pH of the aqueous layer was adjusted to 8.5 with a 25% by weight aqueous sodium hydroxide solution. The aqueous layer was stirred at 75° to 80° C., and thereafter the solution was allowed to separate into two layers, an aqueous layer and an organic layer.

To the organic layer were added 288 g of anhydrous magnesium sulfate and 288 g of activated alumina, and the mixture was stirred at 75° to 80° C. for 15 minutes. Thereafter, anhydrous magnesium sulfate and activated alumina were separated by filtration, and the residue was washed with 1120 g of toluene.

Next, 3000 mL (about 2601 g) of toluene was distilled under reduced pressure, and 9817 g of heptane was added to the residue. The mixture was cooled to −10° to 5° C., stirred at the same temperature for 1 hour, and the mixture was then filtered. The resulting crystals were washed with 1355 g of heptane.

Next, the resulting crystals were dried under reduced pressure of 4 kPa at a temperature of 50° to 60° C., to give 1291 g of a crude mirtazapine having an HPLC purity of 99.8%.

Preparation Example 2

Preparation of Crude Mirtazapine

A reactor was charged with 270 kg of concentrated sulfuric acid under a nitrogen gas stream, and thereafter 75 kg of 2-(4-methyl-2-phenylpiperazin-1-yl)pyridine-3-methanol was added to the flask in divided portions at 0° to 30° C., and the mixture was stirred at 30° to 40° C. for 8 hours.

The resulting reaction solution was added in a thin stream to 540 kg of water at a temperature of 0° to 30° C. The inside of the reaction tank was washed with 34 kg of concentrated sulfuric acid, and the obtained washed liquid was mixed with a reaction mixture obtained above.

Next, the pH of this reaction solution was adjusted to about 1 to 2 with 25% by weight aqueous sodium hydroxide solution, and 29 kg of decolorizing carbon (50% wet product) was added to the reaction mixture. The mixture was stirred for 1 hour, and thereafter filtered. The decolorizing carbon was washed with 143 kg of water, and the washed solution was mixed with the filtrate. To the filtrate was added 98 kg of toluene, and the mixture was washed at 25° to 35° C.

The solution was allowed to separate into two layers, an aqueous layer and an organic layer, at 25° to 35° C. To the aqueous layer was added 130 kg of toluene, and the pH of the aqueous layer was adjusted to 9 with a 25% by weight aqueous sodium hydroxide solution. The aqueous layer was stirred at 75° to 80° C., and thereafter the solution was allowed to separate into two layers, an aqueous layer and an organic layer.

To the organic layer were added 351 kg of toluene, and thereafter 13 kg of anhydrous magnesium sulfate and 13 kg of activated alumina (commercially available from Sumitomo Chemical Co., Ltd. under the trade name of A-11) at 30° to 40° C., and the mixture was stirred at the same temperature for 1 hour. The organic layer was filtered at 30° to 40° C., and the residue was washed with 43 kg of toluene. The washed solution was mixed with the filtrate, and toluene was distilled under reduced pressure of 5 to 40 kPa at a temperature of 30° to 80° C. The amount of toluene distilled was 530 L. To the residue was added 427 kg of heptane at 60° to 80° C., and a small amount of seed crystals were added at about 50° C., and the mixture was cooled to −10° to 5° C. The mixture was stirred at the same temperature for 1 hour, and thereafter filtered. The obtained crystals were washed with 76 kg of heptane cooled to −10° to 5° C. The crystals were further washed under reduced pressure at 40° to 50° C., to give 56 kg of a crude mirtazapine having HPLC purity of about 99%. The yield was 79.7%.

Example 1

In 510.6 g of methanol of 0° to 5° C. was dissolved 129.1 g of the crude mirtazapine obtained in Preparation Example 1, and 1.3 g of decolorizing carbon was added thereto at 0° to 5° C. The mixture was then stirred for 15 minutes. The mixture was filtered at 0° to 5° C. to remove lower alcohol insolubles. Thereafter, methanol was distilled from the resulting filtrate under reduced pressure of 40 to 50 kPa until its internal temperature reached 50° C. The distilled amount of methanol was 490 g.

Next, 582.8 g of heptane was added to the methanol-distilled filtrate, and methanol was azeotropically distilled until the internal temperature reached 73° C. As a result, 270 g of methanol-containing heptane was distilled. The concentrate was then cooled to −10° to 5° C., and stirred at the same temperature for 1 hour. The concentrate was filtered, and the resulting crystals were washed with 176.6 g of heptane. Thereafter, the crystals were dried under reduced pressure of 4 kPa at 60° C., to give 103.3 g of anhydrous mirtazapine crystals. The yield was 80%. The particle diameter of the resulting anhydrous mirtazapine crystals was too large to be measured with a laser diffraction particle size analyzer. The particle diameter was approximately 200 to 300 μm. In the anhydrous mirtazapine crystals, heptane remained in an amount of 1010 ppm.

A portion of the resulting anhydrous mirtazapine crystals was taken, and the anhydrous mirtazapine crystals were added to methanol having a volume of 10-fold the volume of the anhydrous mirtazapine crystals at a temperature of 20° to 30° C. to dissolve anhydrous mirtazapine crystals. The absorbance of the methanol solution at a wavelength of 600 nm was then determined, and found to be not more than 0.1. It was confirmed from this finding that the anhydrous mirtazapine crystals were substantially free of lower alcohol insolubles.

Next, the anhydrous mirtazapine crystals were pulverized with a pulverizer [atomizer (pulverizer), having 12 hammers and a screen having openings of 1 mm] at 45 Hz at a rotational speed of 5175 rpm, so that the average particle diameter was reduced to about 20 μm, to give 100 g of white powder of white anhydrous mirtazapine crystals (anhydrous mirtazapine) (pulverization yield: 97%). A microphotograph of the resulting anhydrous mirtazapine is shown in FIG. 1, at 500×.

The amount of residual solvent in the resulting anhydrous mirtazapine was then examined. As a result, the content of heptane, a residual solvent, was found to be 180 ppm. It was confirmed from this finding that the anhydrous mirtazapine contained substantially no residual solvent.

The physical properties of the resulting anhydrous mirtazapine were as follows.

(1) HPLC purity: 99.98%
(2) Melting point: 114° to 116° C.
(3) Bulk density: 0.3 g/mL Example 2

To 198 kg of methanol of 0° to 5° C. was added 50 kg of the crude mirtazapine obtained in Preparation Example 2 with stirring, and 0.5 kg of decolorizing carbon was added thereto at 0° to 5° C. The mixture was then stirred for 1 hour. The filtering device was pre-coated with 11.5 kg of activated clay (commercially available from MIZUSAWA INDUSTRIAL CHEMICALS, LTD. under the trade name of V2, granularity: 5 to 60 mesh, specific surface area: 150 to 300 m$^2$/g). Thereafter, the resulting mixture was filtered at 0° to 5° C., and the residue was washed with 24 kg of methanol at 0° to 5° C. Thereafter, methanol was distilled from the resulting filtrate under reduced pressure of 4 to 55 kPa until the internal temperature reached 50° C. The distilled amount of methanol was 161 L.

306 kg of heptane was then added to the methanol-distilled filtrate, and methanol was azeotropically distilled until the internal temperature reached 75° C. As a result, 230 L of methanol-containing heptane was distilled.

When this concentrate was gradually cooled, crystallization occurred at about 58° C. The mixture was stirred at the same temperature for 1 hour, was subsequently cooled to −10° to 5° C., and stirred at that temperature for another 1 hour. Thereafter, the resulting anhydrous mirtazapine crystals were filtered, and washed with 137 kg of heptane at 0° to 5° C.

The anhydrous mirtazapine crystals were dried at 60° C. under reduced pressure. After the internal temperature became constant, the crystals were dried at 90° to 95° C. The particle diameter of the resulting anhydrous mirtazapine crystals was too large to be measured with a laser diffraction particle size analyzer. The particle diameter was approximately 200 to 300 μm. The yield of the anhydrous mirtazapine crystals was 38 kg (yield: 76.0%).

A portion of the resulting anhydrous mirtazapine crystals was taken, and the anhydrous mirtazapine crystals were added to methanol having a volume of 10-fold of the volume of the anhydrous mirtazapine crystals at a temperature of 20° to 30° C. to dissolve the anhydrous mirtazapine. The absorbance of the methanol solution at a wavelength of 600 nm was then determined, and found to be not more than 0.1. It was confirmed from this finding that the anhydrous mirtazapine crystals contained substantially no lower alcohol insolubles.

Next, the anhydrous mirtazapine crystals were pulverized with a pulverizer [atomizer (pulverizer), having 12 hammers and a screen having openings of 1 mm] at 45 Hz at a rotational speed of 5175 rpm. The average particle diameter of the resulting pulverized anhydrous mirtazapine was found to be about 20 μm.

The amount residual solvent of the resulting anhydrous mirtazapine was then examined. As a result, the content of heptane, which was a residual solvent, was found to be 92 ppm. It was confirmed from this finding that the anhydrous mirtazapine contained substantially no residual solvent.

The physical properties of the resulting anhydrous mirtazapine were as follows.

(1) HPLC purity: 99.99%
(2) Melting point: 114° to 116° C.
(3) Trapped density: 0.17 g/mL
    Bulk density: 0.45 g/mL Comparative Example 1

Ten grams of the crude mirtazapine obtained in Preparation Example 1 was dissolved in 200 g of a petroleum ether with heating. The mixed solution was decolorized with 500 mg of decolorizing carbon, and the mixture was filtered, and the filtrate was then cooled to 0° to 5° C. to allow precipitation. Thereafter, the mixture was filtered to collect crystals, and the crystals were dried, to give 8.1 g of mirtazapine. From the findings that the hue of mirtazapine was pale yellow, and that the absorbance was not more than 1.6, it was confirmed that the mirtazapine contained insolubles which did not dissolve in methanol. HPLC Purity of this mirtazapine was 99.8%.

Next, the amount of the residual solvent of the resulting mirtazapine was examined. As a result, the content of heptane, which was a residual solvent, was found to be 1100 ppm. In addition, the average particle diameter of the mirtazapine was examined. However, the average particle diameter was too large to be measured with a laser diffraction particle size analyzer.

Comparative Example 2

Ten grams of the crude mirtazapine obtained in Preparation Example 1 was dissolved in 50 g of tert-butyl methyl ether with heating. The mixed solution was decolorized with 500 mg of decolorizing carbon, and the mixture was filtered. The filtrate was concentrated by distilling 35 g of tert-butyl methyl ether. The concentrate was cooled to 0° to 5° C. to allow precipitation.

The resulting mirtazapine crystals were filtered and dried, to give 8.6 g of mirtazapine crystals. From the findings that the hue of the resulting mirtazapine crystals was pale yellow and that the absorbance was 2.42, it was confirmed that the mirtazapine contained insolubles which did not dissolve in methanol. HPLC Purity of this mirtazapine was 99.8%.

Also, the resulting mirtazapine crystals were not for practical use because the odor of tert-butyl methyl ether was strong.

The anhydrous mirtazapine crystals of the present invention, substantially free of lower alcohol insolubles and the anhydrous mirtazapine having an average particle diameter of 10 to 50 μm substantially free of no residual solvent, are preferably used for pharmaceuticals, particularly in light of the high degree of purity due to the substantially freedom of lower alcohol insolubles or residual solvent.

In addition, according to the process of the present invention, anhydrous mirtazapine having high purity can be efficiently and industrially prepared from a crude mirtazapine.

The present application is based on Japanese Patent Application No. 2000-359891, filed in the Japanese Patent Office on Nov. 27, 2000, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. An anhydrous mirtazapine crystal substantially free of lower alcohol insolubles.

2. A process for preparing an anhydrous mirtazapine crystal, comprising:
    filtering a lower alcohol solution of crude mirtazapine to provide a filtrate;
    concentrating the filtrate to provide a concentrated filtrate; and
    crystallizing anhydrous mirtazapine from said concentrated filtrate using a precipitation solvent selected from the group consisting of heptane and petroleum ethers.

3. The process according to claim 2, further comprising an initial step of forming the lower alcohol solution of crude mirtazapine by dissolving crude mirtazapine in a lower alcohol.

4. The process according to claim 3, wherein the lower alcohol in said forming step has a temperature of from −5° to 10° C.

5. The process according to claim 4, wherein the lower alcohol is used in said forming step in an amount of from 300 to 500 parts by weight based on 100 parts by weight of the crude mirtazapine.

6. The process according to claim 2, wherein the lower alcohol is a member selected from the group consisting of methanol, ethanol, propanol and isopropanol.

7. The process according to claim 6, wherein the lower alcohol is methanol.

8. The process according to claim 3, wherein the lower alcohol is a member selected from the group consisting of methanol, ethanol, propanol and isopropanol.

9. The process according to claim 2, wherein the precipitation solvent is used in an amount of from 300 to 600 parts by weight based on 100 parts by weight of the crude mirtazapine.

10. The process according to claim 4, wherein the lower alcohol of said forming step has a temperature of from 0 to 5° C.

11. The process according to claim 3, further comprising after said forming step, decolorizing said lower alcohol solution of crude mirtazapine.

12. The process according to claim 11, wherein said decolorizing is performed by contacting the lower alcohol solution with a decolorizing agent, followed by separating the decolorizing agent from the lower alcohol solution.

13. The process according to claim 11, wherein said decolorizing is performed using a decolorizing agent selected from the group consisting of decolorizing carbon, activated alumina, activated clay and mixtures thereof.

14. The process according to claim 2, wherein said filtering is performed by reduced pressure filtering or pressure filtration.

15. The process according to claim 2, wherein said concentrating is performed by reduced pressure distillation.

16. The process according to claim 2, further comprising distilling precipitation solvent from the crystallizing step to maximize precipitation of anhydrous mirtazapine.

17. The process according to claim 2, further comprising drying the anhydrous mirtazapine obtained.

18. The process according to claim 17, wherein said drying is performed under reduced pressure.

19. Anhydrous mirtazapine having an average particle diameter of 10 to 50 $\mu$m and substantially free of residual solvent.

20. A process for preparing anhydrous mirtazapine having an average particle diameter of 10 to 50 $\mu$m and substantially free of residual solvent, comprising pulverizing anhydrous mirtazapine crystals to an average particle diameter of 10 to 50 $\mu$m.

21. The process of claim 20, wherein said pulverizing is performed using a member selected from the group consisting of hammer-mills, cutter mills and atomizers.

22. A process for preparing an anhydrous mirtazapine crystal, comprising:
    a step of filtering a lower alcohol solution of crude mirtazapine to provide a filtrate;
    a step of concentrating the filtrate to provide a concentrated filtrate; and
    a step of crystallizing anhydrous mirtazapine from said concentrated filtrate using a precipitation solvent selected from the group consisting of heptane and petroleum ethers.

23. The process according to claim 22, further comprising, prior to said step of filtering, a step of forming the lower alcohol solution of crude mirtazapine.

24. The process according to claim 23, wherein said step of forming step uses a lower alcohol having a temperature of from −5° to 10° C.

25. The process according to claim 24, wherein the lower alcohol is used in said step of forming in an amount of from 300 to 500 parts by weight based on 100 parts by weight of the crude mirtazapine.

26. The process according to claim 22, wherein the lower alcohol is a member selected from the group consisting of methanol, ethanol, propanol and isopropanol.

27. The process according to claim 26, wherein the lower alcohol is methanol.

28. The process according to claim 23, wherein the lower alcohol is a member selected from the group consisting of methanol, ethanol, propanol and isopropanol.

29. The process according to claim 22, wherein the precipitation solvent is used in an amount of from 300 to 600 parts by weight based on 100 parts by weight of the crude mirtazapine.

30. The process according to claim 24, wherein the lower alcohol of said step of forming step has a temperature of from 0° to 5° C.

31. The process according to claim 23, further comprising after said step of forming, a step of decolorizing said lower alcohol solution of crude mirtazapine.

32. The process according to claim 31, wherein said step of decolorizing is performed by contacting the lower alcohol solution with a decolorizing agent, followed by a step of separating the colorizing agent from the lower alcohol solution.

33. The process according to claim 31, wherein said step of decolorizing is performed using a decolorizing agent selected from the group consisting of decolorizing carbon, activated alumina, activated clay and mixtures thereof.

34. The process according to claim 22, wherein said step of filtering is performed by reduced pressure filtering or pressure filtration.

35. The process according to claim 22, wherein said step of concentrating is performed by reduced pressure distillation.

36. The process according to claim 22, further comprising a step of distilling precipitation solvent from the step of crystallizing.

37. The process according to claim 22, further comprising a step of drying the anhydrous mirtazapine obtained.

38. The process according to claim 37, wherein said step of drying is performed under reduced pressure.

39. A process for preparing anhydrous mirtazapine having an average particle diameter of 10 to 50 $\mu$m and substantially free of residual solvent, comprising a step of pulverizing anhydrous mirtazapine crystals to an average particle diameter of 10 to 50 $\mu$m.

* * * * *